(12) United States Patent
Shoichet et al.

(10) Patent No.: US 6,887,658 B2
(45) Date of Patent: May 3, 2005

(54) METHODS OF IDENTIFYING NON-SPECIFIC INHIBITORS OF BIOMOLECULES

(75) Inventors: Brian K. Shoichet, Chicago, IL (US); Susan L. McGovern, Chicago, IL (US)

(73) Assignee: Northwestern University, Evanston, IL (US)

(*) Notice: Subject to any disclaimer, the term of this patent is extended or adjusted under 35 U.S.C. 154(b) by 39 days.

(21) Appl. No.: 10/171,814

(22) Filed: Jun. 14, 2002

(65) Prior Publication Data

US 2004/0234942 A1 Nov. 25, 2004

Related U.S. Application Data

(60) Provisional application No. 60/298,527, filed on Jun. 15, 2001.

(51) Int. Cl.[7] ................................................ C12Q 1/00
(52) U.S. Cl. .......................................................... 435/4
(58) Field of Search ............................................ 435/4

(56) References Cited

PUBLICATIONS

Luo, et al., The Elongation Domain of ELL is Dispensible but its ELL–Associated Factor 1 Interaction Domain is Essential for MLL–ELL–Induced Leukemogenesis, Molecular and Cellular Biology, 21:5678–5687 (2001).

Miller, et al., Ligand Binding to Proteins: The Binding Landscape Model, Protein Sci., 6:2166–2179 (1997).

Patera, et al., Crystal Structures of Substrate and Inhibitor Complexes with AmpC β–Lactamase: Possible Implications for Substrate–Assisted Catalysis, J. Am. Chem. Soc. 122: 10504–10512 (2000).

Rishton, G.M., Reactive Compounds and in vitro False Positives in HTS, Drug Discovery Today, 2: 382–384 (1997).

Roche, et al., Development of a Virtual Screening Method for Identification of "Frequent Hitters" in Compound Libraries, J. Med. Chem. 45: 137–142 (2002).

Stopa, et al., Supramolecular Ligands: Monomer Structure and Protein Ligation Capability, Biochimie, 80:963–968 (1998).

Luo et al., Molecular and Cellular Biology, 21:5678–5687 (2001).

Miller et al., Protein Sci., 6:2166–2179 (1997).

Patera et al., 122:10504–10512 (2000).

Rishton, Drug Discovery Today, 2:382–384 (1997).

Roche et al., J. Med. Chem., 45:137–142 (2002).

Stopa et al., Biochimie, 80:963–968 (1998).

*Primary Examiner*—Sandra E. Saucier
(74) *Attorney, Agent, or Firm*—Klauber & Jackson

(57) ABSTRACT

The present invention provides methods of identifying compounds that non-specifically inhibit biological reactions. The present invention further includes kits that facilitate this identification. In addition, complications of compounds for use in high throughput drug screening that have been evaluated by the disclosed methodology are also part of the present invention. Further, the invention provides methods for identifying a false positive compound previously identified as positive in a screening assay by measuring the activity of at least one biological activity in the presence and absence of a small molecule compound capable of inhibiting aggregate formation, e.g., digitonin.

4 Claims, 2 Drawing Sheets

Fig. 1
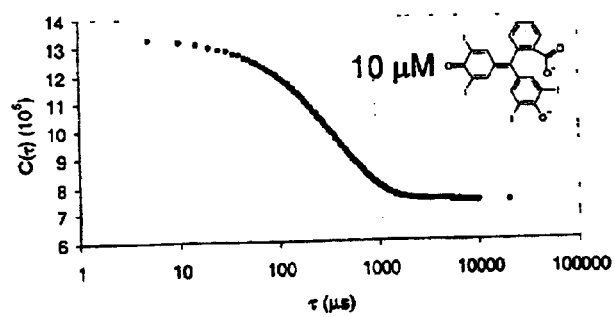
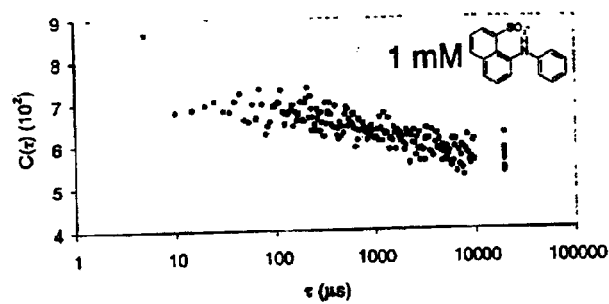
Fig. 2

METHODS OF IDENTIFYING NON-SPECIFIC INHIBITORS OF BIOMOLECULES

This application claims the benefit of U.S. provisional application No. 60/298,527.

GOVERNMENTAL SUPPORT

The research leading to the present invention was supported, at least in part, by a grant from the National Institutes of Health, GM59957. Accordingly, the Government may have certain rights in the invention.

FIELD OF THE INVENTION

The present invention relates to methods of identifying compounds that non-specifically inhibit or antagonize biological macromolecules. The identification of such compounds allows their removal from screening and/or compound libraries thereby increasing the efficiency of high throughput and virtual drug screens used for selecting lead compounds for drug discovery. Kits facilitating such identification are also included, as are compound and screening libraries that have been analyzed by the disclosed methodology.

BACKGROUND

To discover new lead compounds for drug design, large libraries of chemicals are screened for their ability to modulate the function of a particular target biomacromolecule (e.g., a receptor, or enzyme). High-throughput screening (HTS) and virtual screening are two methods of discovering new lead compounds that are currently widely employed in drug design. In the latter case, the computational "hits" are then verified experimentally.

These screening methods have been used to identify novel molecules that are dissimilar to known ligands of the specific target, but nevertheless bind to that target at micromolar or even sub-micromolar concentrations. However, often, on detailed investigation, many of the novel "hits" are found to be false positives, ie., the inhibitor is found to be non-specific. A hit can be categorized as a "false positive" for many reasons. Among the largest classes of false positives are those molecules that act non-specifically, that have undefined mechanisms of inhibition, and/or that have unusual and undesired kinetic properties. Such non-specific inhibitors artificially inflate hit rates in both virtual and experimental screening projects, and lead investigators to follow the wrong trail. This can waste enormous time and resources. Unfortunately, heretofore, there has been no reliable method of identifying a compound as a non-specific inhibitor.

There is a need to provide a method of detecting false positives early in the discovery process methodology. In addition, there is a need to provide compound/screening libraries that are essentially free of compounds that lead to such false positives, as well as methods that can be used to identify such compounds in a drug library.

SUMMARY OF THE INVENTION

The present invention provides a method of identifying a compound that is likely to act as a false positive in a screen for lead compounds, e.g., for drug discovery. Accordingly, in a first aspect, the invention features a method of identifying a false positive in a screening assay, comprising identifying a compound having one or more of the following characteristics:

(i) inhibition of unrelated biomacromolecules, for example, inhibition of unrelated enzymes;

(ii) time-dependent inhibition, for example, if pre-incubating an enzyme with the compound prior to performing the catalytic reaction leads to an increase in the inhibitory effect (a decrease in $IC_{50}$);

(iii) decreasing inhibitory effect with increasing ionic strength of the biological reaction solution;

(iv) decreasing inhibitory effect as the molar ratio of the enzyme to the compound increases; e.g., its $IC_{50}$ value markedly increases in the presence of a 10-fold increase in enzyme;

(v) non-competitive inhibition; and (vi) formation of particles in solution that can be detected by Dynamic Light Scattering (DLS) and/or Tranmission Electron Microscopy (TEM).

One such embodiment comprises measuring the activity of a first biological reaction in the presence and absence of the compound, and measuring the activity of an unrelated second biological reaction in the presence and absence of the compound. When the activity of both the first and second biological reactions are inhibited in the presence of the compound relative to in its absence, the compound is identified as a compound that is likely to be a false positive in a drug screening assay. In another embodiment, the method further comprises measuring the activity of an unrelated third biological reaction in the presence and absence of the compound. In a preferred embodiment, the activity of an unrelated fourth biological reaction is also performed in the presence and absence of the compound. When the activity of the first, second, third, and fourth unrelated biological reactions are all inhibited in the presence of the compound relative to in its absence, the compound is identified as a compound that is likely to be a false positive in a drug screening assay. In still another embodiment, the activity of an unrelated fifth to tenth biological reaction is included in the assay protocol. As above, when the activity of all of the unrelated biological reactions measured are all inhibited in the presence of the compound relative to in the absence of the compound, the compound is identified as a compound that is likely to be a false positive in a drug screening assay.

In a preferred embodiment, the first and second unrelated biological reactions (and/or additional unrelated biological reactions) are enzyme reactions. In particular embodiment of this type, the method further comprises repeating the first and second unrelated biological reactions (and/or additional unrelated biological reactions) in the presence of a two-fold or greater increased concentration of the enzymes (and preferably five-fold or greater, and more preferably ten-fold to fifty-fold increased concentration of the enzymes). When the activity of both the first and second unrelated biological reactions (and/or additional unrelated biological reactions) are inhibited in the presence of the compound relative to in its absence, and the amount of inhibition is decreased in the presence of a two-fold or greater increased concentration of the enzymes (or five-fold or greater, or ten-fold to fifty-fold increased concentration of the enzymes), the compound is identified as a compound that is likely to act as a false positive in a drug screening assay.

In another embodiment, the method further comprises repeating the first and second biological reactions over a four-fold range of (increased) ionic strength (and preferably over a 25-fold range or greater, and more preferably over a 100-fold to 500-fold range of ionic strength or greater). When the amount of inhibition of the biological reaction by the compound decreases over a four-fold range of ionic strength (or over a 25-fold range or greater, or over a 100-fold to 500-fold range of ionic strength or greater), the compound is identified as a compound that acts as a false positive in a drug screening assay.

The present invention also provides a method of identifying a compound from a compilation of compounds as a false positive candidate. One such method comprises measuring the activity of two, three, or four (and preferably five to ten or more) unrelated biological reactions in the presence of the compound. When the activity of all of the unrelated biological reactions measured are inhibited by the compound, the compound is identified as a false positive candidate. An alternative embodiment comprises measuring the activity of two, three, or four unrelated biological reactions (and preferably five to ten or more unrelated biological reactions) in the presence of a group of compounds from a compilation of compounds. When the activity of all the unrelated biological reactions examined are inhibited, the group of compounds is identified as comprising at least one false positive candidate. The activity of the two, three, or four unrelated biological reactions (or the five to ten or more unrelated biological reactions) is then measured the in the presence of each compound of the group. When the activity of all the unrelated biological reactions examined are inhibited by a compound, the compound is identified as a false positive candidate.

In one embodiment, the group of compounds contains between 2 and 250 compounds. In a more specific embodiment, the group of compounds contains about 100 compounds. In a more preferred embodiment, the group contains between 5 and 50 compounds.

In a preferred embodiment, the first and second unrelated biological reactions (and/or additional unrelated biological reactions) are enzyme reactions. In particular embodiment of this type, the method further comprises repeating the first, and second unrelated biological reactions (and/or additional unrelated biological reactions) in the presence of a two-fold or greater increased concentration of the enzymes (preferably five-fold or greater, and more preferably ten-fold to 50-fold increased concentration of the enzymes). When the activity of both the first and second unrelated biological reactions (and/or additional unrelated biological reactions) are inhibited in the presence of the compound relative to in its absence, and the amount of inhibition is decreased in the presence of a two-fold or greater increased concentration of the enzymes (or five-fold or greater, or ten-fold to 50-fold increased concentration of the enzymes), the compound is identified as a compound that is a false positive candidate.

In another embodiment, the method further comprises repeating the first, and second biological reactions over a four-fold range of (increased) ionic strength (preferably over a 25-fold range or greater, and more preferably over a 100-fold to 500-fold range of ionic strength or greater). When the amount of inhibition of the biological reaction by the compound decreases over the four-fold range of (increased) ionic strength (or over the 25-fold range or greater, or the 100-fold to 500-fold range of ionic strength or greater), the compound is identified as a compound that is a false positive candidate.

The present invention further provides a compilation of compounds that has had removed at least one false positive candidate identified by a method of the present invention. In a preferred embodiment, the compilation of compounds has had multiple false positive candidates removed that have been identified by a method of the present invention. In a more preferred embodiment, the compilation of compounds has had all of the false positive candidates removed that have been identified by a method of the present invention.

The present invention also provides a method of distinguishing a non-specific inhibitor from a specific inhibitor. One such method comprises measuring the activity of two unrelated biological reactions in the presence of an inhibitor of a test reaction. The inhibitor is identified as a specific inhibitor if it does not inhibit the activity of a set of two unrelated biological reactions, whereas the inhibitor is identified as a non-specific inhibitor if it does inhibit the activity of the set of two unrelated biological reactions. In a preferred embodiment, the method further comprises measuring the activity of an unrelated third biological reaction in the presence of the inhibitor of the test reaction. In a more preferred embodiment, the activity of an unrelated fourth biological reaction is also performed in the presence of the inhibitor of the test reaction. The inhibitor is identified as a specific inhibitor if it does not inhibit the activity of a set of three and/or four unrelated biological reactions, whereas the inhibitor is identified as a non-specific inhibitor if it does inhibit the activity of the set of three and/or four unrelated biological reactions. In still another embodiment, the activity of an unrelated fifth to tenth (or more) biological reaction(s) is included in the assay protocol.

In a preferred embodiment, the first and second unrelated biological reactions (and/or additional unrelated biological reactions) are enzyme reactions. In a particular embodiment of this type, the method further comprises repeating the first and second unrelated biological reactions (and/or additional unrelated biological reactions) in the presence of a two-fold or greater increased concentration of the enzymes (preferably five-fold or greater, and more preferably ten-fold to 50-fold increased concentration of the enzymes). When the activity of both the first and second unrelated biological reactions (and/or additional unrelated biological reactions) are inhibited in the presence of the inhibitor, and the amount of inhibition is decreased in the presence of a two-fold or greater increased concentration of the enzymes (or five-fold or greater, or ten-fold to 50-fold increased concentration of the enzymes), the inhibitor is identified as a non-specific inhibitor.

In another embodiment, the method further comprises repeating the first and second biological reactions over a four-fold range of (increased) ionic strength (and preferably over a 25-fold or greater, and more preferably over a 100-fold to 500-fold range ionic strength or greater). When the amount of inhibition of the biological reaction by the inhibitor decreases over the four-fold range of (increased) ionic strength (or 25-fold or greater, or 100-fold to 500-fold range of ionic strength or greater), the inhibitor is identified as a non-specific inhibitor.

All of the methods disclosed herein can further comprise measuring the activity of the first and second unrelated biological reactions (and/or additional unrelated biological reactions) with a known aggregative compound. When the known aggregative compound has the same effect on the biological reactions as the compound (and/or inhibitor) being studied, the compound being studied is identified as a compound that is likely to act as a false positive (e.g., non-specific inhibitor) in a drug screening assay. In a preferred embodiment, further studies as outlined below, such as Dynamic Light-Scattering (DLS), or size exclusion assays, are included to identify a compound (and/or inhibitor) as an aggregative compound.

Further, all of the methods disclosed herein can further comprise measuring the activity of the first and second unrelated biological reactions (and/or additional unrelated biological reactions) in the presence and absence of a small molecule compound capable of inhibiting aggregate formation. A compound exhibiting inhibiting of unrelated biological reactions in the absence, but not the presence, of the small molecule compound is identified as a false positive candidate. In one embodiment, the biological reactions are enzymatic reactions. In another embodiment, the small molecule compound capable of inhibiting aggregate formation is selected from the group consisting of digitonin, saponin, polymixin B, amphotericin, nystatin, an aminoglycoside, and Triton X-100™. In a more specific embodiment, the small molecule compound is digitonin.

One related aspect of the invention is based on the discovery that specific small molecule compounds are capable of disrupting aggregate-based inhibitors. Accordingly, the present invention provides a method of identifying a positive compound identified in a screen for lead compounds as a false positive. In one aspect, the invention features a method of identifying a false positive candidate previously identified as positive in a screening assay, comprising measuring the ability of a false positive candidate compound to inhibit unrelated biomacromolecules in the absence but not the presence of a small molecule compound capable of inhibiting aggregate formation. A false positive candidate will exhibit inhibition of unrelated molecules, such as enzymes, in the absence but not the presence of a small molecule compound capable of inhibiting aggregate formation. In one embodiment, the biomacromolecules are enzymes. In another embodiment, the small molecule compound capable of inhibiting aggregate formation is selected from the group consisting of digitonin, saponin, polymixin B, amphotericin, nystatin, an aminoglycoside, and Triton X-100™. In a more specific embodiment, the small molecule compound is digitonin.

Another aspect of the present invention provides a kit for determining whether an agent is a false-positive candidate in a drug screening assay. One such kit comprises two or more enzymes that are separately packaged, substrates and cofactors required to allow the measurement of the activity of the enzymes, and one or more aggregative compounds as a control. In a preferred embodiment, the kit comprises a small molecule compound capable of inhibiting aggregate formation. In a more preferred embodiment, the small molecule compound is digitonin.

In one embodiment, the kit comprises three, four or more (e.g., five to ten) enzymes that are packaged separately from each other along with their corresponding substrates and cofactors. In a particular embodiment, the kit further comprises instructions for determining the activity of the enzymes. In another embodiment, the kit further comprises instructions for determining whether a compound is an aggregative compound. In a preferred embodiment, the kit further comprises multiple concentrations/amounts of the enzymes packaged separately from each other along with their corresponding substrates and cofactors.

The present invention further provides a solid support (e.g., a plate) composed of compartments that contain the reagents for measuring a specific biological activity and in which at least four of the compartments contain the reagents for measuring a different unrelated biological activity. In a particular embodiment, at least four of the unrelated biological activities are catalyzed by a corresponding unrelated enzyme. In one embodiment, each biological activity is measured with and without the presence of a small molecule compound capable of inhibiting aggregate formation. In a more specific embodiment, the small molecule is digitonin. When an enzymatic assay is performed in the presence of a solid support comprising digitonin, digitonin is solubilized and prevents aggregate formation. Thus assays run in parallel with and without digitonin readily identify a false positive where inhibition of unrelated biological activities results from aggregate formation.

Preferably the solid support comprises individual compartments that contain different concentrations of the same enzyme. In another embodiment, the solid support comprises individual compartments that contain the same reaction, but are designed to be performed at different ionic strengths as disclosed above.

The present invention further provides a method of using a solid support of the present invention to identify a compound from a compilation of compounds as a false positive candidate. Any of the methods described herein may be performed with the aid of such solid supports. In one such embodiment the method comprises measuring the activity of four unrelated biological reactions in the presence of the compound with the solid support. When the activity of all four unrelated biological reactions of the solid support are inhibited by the compound, the compound is identified as a false positive candidate. In another embodiment, the solid support allows biological reactions to be conducted in parallel with and without a small molecule inhibitor of aggregate formation. In another embodiment, the solid support comprises individual compartments that contain different concentrations of the same enzyme. When the activity of the biological reactions of the solid support are inhibited to a lesser degree by the compound as the concentration of the enzyme increases, the compound is identified as a false positive candidate. In still another embodiment, the solid support comprises individual compartments that contain the same reaction, but are designed to be performed at different ionic strengths. When the activity of the biological reactions of the solid support are inhibited to a lesser degree by the compound as the ionic strength increases, the compound is identified as a false positive candidate.

Other objects and advantages will become apparent from a review of the ensuing detailed description taken in conjunction with the following illustrative drawing.

BRIEF DESCRIPTION OF THE DRAWINGS

FIGS. 1–2 show the autocorrelation functions (ACFs) from dynamic light scattering (DLS). FIG. 1 is with 10 $\mu$M tetraiodophenolphthalein in 50 mM $KP_i$. The high-intensity well-defined ACF suggests the presence of particles.

FIG. 2 is with 1 mM ANS in 50 mM $KP_i$. The low-intensity, poorly-defined ACF suggests the absence of particles. The laser power and integration times for the experiments in FIGS. 1 and 2 are comparable.

DETAILED DESCRIPTION

Figure 3:
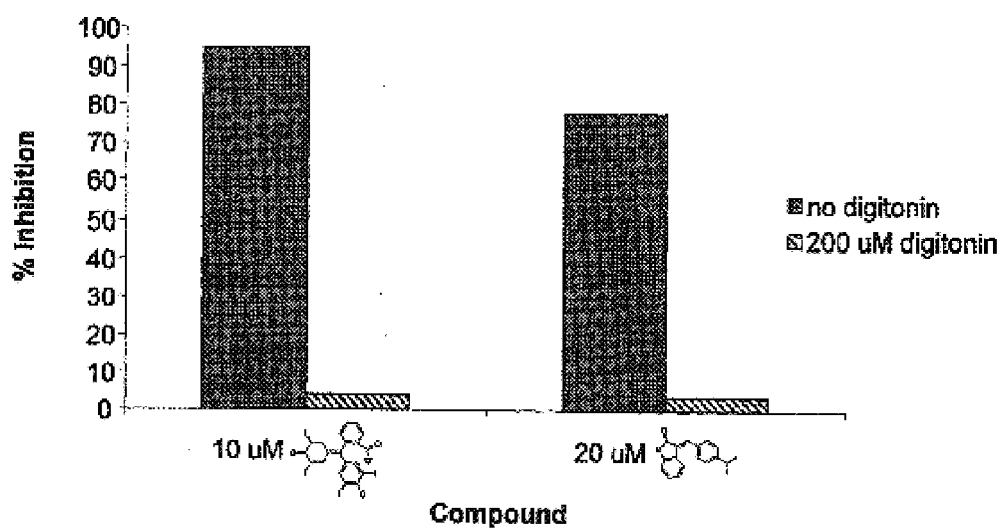
FIG. 3 is a bar graph of the effect of digitonin in decreasing inhibition by aggregate forming, non-specific screening hits. Dark=no digitonin; striped=200 $\mu$M digitonin.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

As used herein, a "biological reaction" is a binding and/or catalytic reaction that comprises at least one nucleic acid (RNA or DNA) and/or protein as a binding partner and/or reactant/catalyst. Biological reactions include classical enzyme reactions, (e.g., catalase converting $2H_2O_2$ to $2H_2O+O_2$), protein-ligand binding, (e.g., hemoglobin and $O_2$, or an antibody with its protein target) protein-DNA binding (a transcription factor with its corresponding response element), and DNA-RNA, DNA—DNA and RNA—RNA hybridizations. Biological reactions that take place in a cell (in situ) are also included (e.g., a transcription factor binding to a response element that results in the transcription/translation of a marker protein).

As used herein, one biological reaction is "unrelated" to a second biological reaction (an "unrelated biological reaction") when the mechanism of the first biological reaction is generally accepted by those having skill in the relevant art to be unrelated to the second biological reaction. For example, the catalytic mechanism of chymotrypsin is unrelated to AmpC β-lactamase but is not unrelated to trypsin since both chymotrypsin and trypsin are serine proteases that use the same HIS-ASP-SER catalytic triad.

As used herein, a "biological reaction" is "inhibited" by a compound when the response elicited by a certain amount of ligand or substrate decreases in the presence of that compound (e.g., a decrease in binding affinity or in reaction velocity). The kinetic constants do not necessarily also need to be determined, particularly when the factor measured is consistent with either the binding constant (Kd) increasing or the catalytic constant (Vmax/Km) decreasing.

An "aggregative compound" is one that forms aggregates in solution of a size of 50 nm in diameter or greater, and that can inhibit multiple unrelated enzymes in a manner that can be correlated with the formation of the aggregate. Examples of aggregative compounds are included in Tables 1–4.

A small molecule compound "capable of inhibiting aggregate formation", e.g., such as digitonin and related molecules, disrupts aggregate formation as shown by a reduction in fluorescence scattering and reversal of inhibition obtained with aggregate forming inhibitors. Other small molecule compounds capable of inhibiting aggregate formation include saponin, polymixin B, amphotericin, nystatin, aminoglycosides, and Triton X-100™.

A "false positive" is a compound that inhibits a particular biological reaction, but also inhibits other non-related biological reactions. In a preferred embodiment, a false positive is an aggregative compound. A "false positive candidate" is a compound in which there is evidence (either experimental or through virtual screening) to suggest that the compound is likely to be a false positive.

A "compilation of compounds" is a collection of compounds, including those derived from a phage library that can be used for screening lead compounds (e.g., for drug discovery). Examples are the chemical libraries that have been compiled by the pharmaceutical industry including but not limited to those of Merck, Glaxo SmithKline, Bristol Meyers Squib, Monsanto/Searle, Eli Lilly, Novartis, Pharmacia UpJohn, Aventis, Pfizer, and Hoffman La Roche. However, smaller and/or more specific collections are also meant to be included as a compilation of compounds.

As used herein, a "small organic molecule" is an organic compound, including a peptide or organic compound complexed with an inorganic compound, such as a metal, that has a molecular weight of less than two kilodaltons. In a preferred embodiment, the compounds in the compilation of compounds of the present invention are small organic molecules.

As used herein, the term "approximately" is used interchangeably with the term "about" and signifies that a value is within twenty percent of the indicated value i.e., "about" 100 compounds can be between 80 and 120 compounds.

A "polypeptide" is used interchangably with the term "protein" and denotes a polymer comprising two or more amino acids connected by peptide bonds. Preferably, a polypeptide is further distinguished from a "peptide" with a peptide comprising about fifty or less amino acids, and a polypeptide or protein comprising more than about fifty amino acids.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. When referring to a nucleic acid that is DNA, and more specifically a DNA having a particular nucleotide sequence, both the "sense" strand and the complementary "antisense" strand are intended to be included.

The terms "solid substrate" and "solid support" are used interchangeably and represent a solid material that provides an inert surface that allows a biological reaction to be performed. Solid supports include biological chip plates as exemplified by Rava et al., U.S. Pat. No. 5,874,219, the contents of which are hereby incorporated by reference in their entireties and multi-well (multi-titer) quartz and polystyrene plates. Examples of material that can be used as solid substrates include glass, peptide polymers (e.g., collagen), peptoid polymers, polysaccharides (including commercial beads, e.g., SEPHADEX and the like), carbohydrates, hydrophobic polymers, polymers, tissue culture polystyrene, metals, derivatized plastic films, glass beads, plastic beads, alumina gels, magnetic beads, nitrocellulose, cellulose, and nylon membranes.

General Description

High-throughput and virtual screening are widely used to discover novel leads for drug design. On examination, many screening hits appear non-drug-like—they act noncompetitively, show little relationship between structure and activity, and have poor selectivity. Attempts to develop these peculiar molecules into viable leads are often futile, and much time can be wasted on the characterization of these "phony" hits. Despite their common occurrence, the mechanism of action of these promiscuous molecules remains unknown. To investigate this problem, 45 diverse screening hits were studied. Fifteen of these were previously reported as inhibitors of various receptors, including β-lactamase, malarial protease, dihydrofolate reductase, HIV Tar RNA, thymidylate synthase, kinesin, insulin receptor, tyrosine kinases, farnesyltransferase, gyrase, prions, triosephosphate isomerase, nitric oxide synthase, phosphoinositide 3-kinase, and integrase; 30 were from an in-house screening library of a major pharmaceutical company. In addition to their original targets, 35 of these 45 compounds were shown to inhibit several unrelated model enzymes. These 35 screening hits included compounds, such as fullerenes, dyes, and quercetin, that have repeatedly shown activity against diverse targets. When tested against the model enzymes, the compounds showed time-dependent but reversible inhibition that was dramatically attenuated by albumin, guanidinium, or urea. Surprisingly, increasing the concentration of the model enzymes 10-fold largely eliminated inhibition, despite a 1000-fold excess of inhibitor; a well-behaved competitive inhibitor did not show this behavior. One model to explain these observations was that the active form of the promiscuous inhibitors was an aggregate of many individual molecules. To test this hypothesis, light scattering and electron microscopy experiments were performed. The nonspecific inhibitors were observed to form particles of 30–400 nm diameter by both techniques. In control experiments, a well-behaved competitive inhibitor and an inactive dye-like molecule were not observed to form aggregates. Consistent with the hypothesis that the aggregates are the inhibitory species, the particle size and IC50 values of the promiscuous inhibitors varied monotonically with ionic strength; a competitive inhibitor was unaffected by changes in ionic strength. Unexpectedly, aggregate formation appears to explain the activity of many nonspecific inhibitors and may account for the activity of many promiscuous screening hits. Molecules acting via this mechanism may be widespread in drug discovery screening databases. Recognition of these compounds may improve screening results in many areas of pharmaceutical interest.

One program of hit validation includes initially test screening hits against a 10-fold increase in the concentration of the target protein. Assuming that the concentration of protein remains at catalytic levels, a significant drop in inhibition suggests that the active inhibitor may be an aggregate. Time-dependence, reversibility (dilution, dialysis), and ionic strength are also testable factors. One definitive test is to use a physical technique such as DLS to detect the presence of aggregates in a solution of the inhibitor or TEM, transmission electron microscopy, though these particular techniques are presently more labor-intensive than varying the enzyme concentration, for example.

Thus, the present invention provides methodology that allows the identification of compounds that lead to and/or are likely to lead to false positives in drug screening protocols. Such compounds can be aggregative compounds that have phenomenological and physical signatures that allow them to be identified by the following characteristics, (see also the Example below):

(a) inhibition of unrelated enzymes at typically micromolar to 100 micromolar it concentrations of compound;

(b) time-dependent inhibition, i.e., pre-incubating an enzyme with an aggregative compound prior to performing the catalytic reaction leads to an increase in the inhibitory effect (a decrease in $IC_{50}$).

(c) inhibition inversely related to the ionic strength of the biological reaction solution;

(d) inhibition inversely related to the molar ratio of the enzyme;

(e) particle formation in solution detectable by DLS and/or TEM.

In a preferred embodiment, such a compound is identified by the ability of the compound to inhibit unrelated enzymes in the absence but not the presence of a small molecule compound capable of inhibiting aggregate formation. In a more specifically preferred embodiment, the small molecule compound is digitonin or a related compound.

The present invention provides specific assays for identifying a compound as being an aggregative compound. Such aggregative compounds are non-specific inhibitors that should not be included in drug/lead discovery/compound screening protocols. One such protocol is based on enzyme assays, though as disclosed herein, the methodology of the present invention is far broader than this. Thus, in one assay a compound is included in two or more unrelated enzyme reactions (an assay with four unrelated enzyme reactions is exemplified below). For convenience, it is preferable that the rate of the reactions catalyzed by the individual enzymes be determined in less than ten minutes. The compound is identified as a good candidate to be an aggregative compound if it inhibits all of the enzyme reactions measured (preferably within the approximate compound concentration range of 0.1 μM to 100 μM).

Another criterion is the effect of pre-incubation of the compound prior to beginning the enzyme reaction. The effect of pre-incubating the enzyme with the compound prior to catalysis is therefore determined. An increase in inhibitory effect, i.e., a decrease in $IC_{50}$, is consistent with the compound being an aggregative compound (see e.g., Table 2 below). In another enzyme assay the ionic strength is varied. If the inhibitory effect of the compound decreases, i.e., an increase in $IC_{50}$, with increasing ionic strength then the compound is a good candidate for being an aggregative compound (see e.g., Table 4 below). In still another enzyme assay the concentration of enzyme is varied. If the inhibitory effect of the compound decreases, i.e., an increase in $IC_{50}$, with increasing enzyme concentration, (being careful to keep the reaction under classical steady state kinetic conditions) then the compound also is a good candidate for being an aggregative compound (see e.g., Table 2 below). If the answer to all of the above is yes, then the compound is very likely to be an aggregative compound. Still another criterion is whether the compound forms particles of about 50 to 500 nm in solution. This can be ascertained by performing a DLS or TEM or like analysis. If the compound forms particles of about 50 to 500 nm in solution, then the compound is most probably an aggregative compound. Finally, if the compound has all of these above defined characteristics, then the compound is almost certainly an aggregative compound.

Methods of Obtaining Candidate Compounds

A candidate compound (hit) can be obtained by a number of means, including from a commercially available chemical library or an "in house" pharmaceutical library. Examples of libraries of compounds that are commercially available include the Available Chemicals Directory (ACD,) the Specs and BioSpecs database, the Maybridge database, and the Chembridge database. Examples of pharmaceutical companies with "in house" chemical libraries include Merck, GlaxoSmithKline, Bristol Myers Squibb, Eli Lilly, Novartis, and Pharmacia.

Alternatively, screening compounds can also be synthesized de novo either individually or as combinatorial libraries (Gordon et al. (1994) J. Med. Chem. 37:1385–1401). They may also be obtained from phage libraries. Phage libraries have been constructed which when infected into host E. coli produce random peptide sequences of approximately 10 to 15 amino acids (Parmley and Smith (1988) Gene 73:305–318); Scott and Smith (1990) Science 249:386–390). Once a phage encoding a peptide that can act as a potential drug has been purified, the sequence of the peptide contained within the phage can be determined by standard DNA sequencing techniques. Once the DNA sequence is known, synthetic peptides can be generated which are encoded by these sequences.

If the three-dimensional structure of the polypeptide and/or nucleic acid has been determined, potential inhibitors can be examined through the use of computer modeling using a docking program such as DOCK, GRAM, or AUTODOCK (Dunbrack et al. (1997) Folding & Design 2:2742). This procedure can include computer fitting of potential inhibitors to the protein to ascertain how well the shape and the chemical structure of the potential inhibitor will bind to the protein (Bugg et al. (1993) Scientific American Dec: 92–98; West et al. (1995) TIPS 16:67–74). Computer programs can also be employed to estimate the attraction, repulsion, and steric hindrance of the protein with a potential inhibitor.

Generally, the greater the steric complementarity and the greater the attractive forces, the more potent the potential inhibitor since these properties are consistent with a tighter binding constant. Furthermore, the more specificity in the design of a potential inhibitor, the more likely that the drug will not interact as well with other proteins. This will minimize potential side-effects due to unwanted interactions with other proteins.

Typically known inhibitors of the protein are chosen as good starting points for the modeling process. Systematic modification of selected inhibitors by computer modeling programs can then be performed until one or more potential inhibitors are identified. Such analysis has been shown to be effective in the development of HIV protease inhibitors (Lam et al. (L1994) Science 263: 380–384; Wlodawer et al. (1993) Ann. Rev. Biochem. 62:543–585; Appelt (1993) Perspectives in Drug Discovery and Design 1:23–48; Erickson (1993) Perspectives in Drug Discovery and Design 1:109–128).

For example, Selzer et al. (1997) Exp. Parasitol. 87(3): 212–221) screened the Available Chemicals Directory (a database of about 150,000 commercially available compounds) for potential cysteine protease inhibitors, using DOCK3.5. Based on both steric and force field considerations, they selected 69 compounds. Of these, three had IC50's below 50 μM.

Compounds can be selected as hits, for example, for their ability to inhibit a selected biological reaction. Assays to identify hits (drug screens) can be performed by any number of means including using high throughput techniques and biological chip technology such as exemplified in U.S. Pat. No. 5,874,219, the disclosure of which is hereby incorporated by reference in its entirety. Selected compounds can then be tested by the methods disclosed herein to determine if the inhibition is specific or non-specific (e.g., if the compound is an aggregative compound). The effective compound(s) can then be synthesized in large quantities for use in in vitro and/or in situ assays.

As is readily apparent, a false positive, e.g., an aggregative compound, can lead to fruitless manipulations (both computational and experimental). Therefore the present methodology can be used to ascertain whether a "lead" compound should be used as a focus of a drug development project or whether it should be discarded Biological Reactions Numerous types of biological reactions can be used in the methods of the present invention. Aside from enzyme assays exemplified below, the methods of the present invention can be applied to binding assays. One such example is a protein-ligand assay. Thus a protein-ligand assay can consist of a protein and its antibody, a receptor and its ligand, a transcription factor and its corresponding nucleic acid response element, etc. In a particular embodiment, the protein can be placed and/or coated onto a solid support. Methods for placing the protein on the solid support are well known in the art and include such things as linking biotin to the protein and linking avidin to the solid support. The corresponding ligand is allowed to equilibrate with the bound protein and the compounds are tested to see if they disrupt the protein-ligand binding. Disruption leads to either a faster release of the free ligand which may be expressed as a faster off time, and/or a greater concentration of released ligand. Alternatively, the compound can be co-administered with the ligand.

The ligand may be labeled as described below. For example, in one embodiment radiolabeled ligand is used to measure the effect of a compound on binding. In another embodiment the natural ultraviolet absorbance of the ligand can be used (where appropriate). In yet another embodiment, a Biocore chip (Pharmacia) coated with the protein is used and the change in surface conductivity can be measured. As is readily apparent, the assay could also be performed using a bound ligand and a free protein. Similarly, an RNA-DNA pair, RNA—RNA pair, or DNA—DNA pair could be used in place of the protein-ligand pair. All of such assays can be readily used in conjunction with or in place of the enzyme reactions disclosed below, to demonstrate that a particular compound is either a specific or a non-specific inhibitor.

In another example, a protein-antibody binding pair can be employed. For convenience, the antibody (ies) to the protein will be referred to herein as $Ab_1$ and antibody (ies) raised in another species as $Ab_2$. The protein can be directly detectable or labeled with a detectable label, the antibody $Ab_1$ can be labeled with a detectable label, and/or the antibody $Ab_2$ can be labeled with a detectable label. The procedures may be summarized by the following equations wherein the asterisk indicates that the particle is labeled, and "X" stands for the protein:

$$X^* + Ab_1 = X^*Ab_1$$

$$X + Ab_1^* = XAb_1^*$$

$$X + Ab_1 + Ab_2^* = XAb_1Ab_2^*$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure. In each instance, the protein forms complexes with one or more antibody (ies) or binding partners and one member of the complex is labeled with a detectable label. The fact that a complex has formed and, if desired, the amount thereof, can be determined by known methods applicable to the detection of labels.

It will be seen from the above that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and the claims, $Ab_1$ will be referred to as a primary or anti-protein antibody, and $Ab_2$ will be referred to as a secondary or anti-$Ab_1$ antibody.

An in situ assay useful and contemplated in accordance with the present invention is known as a "cis/trans" assay. Briefly, this assay employs two genetic constructs, one of which is typically a plasmid that continually expresses a particular receptor that is transfected into an appropriate cell line, and the second of which is a plasmid that expresses a reporter such as luciferase, under the control of the receptor. Thus, one of the plasmids would be a construct that results in expression of the receptor in the chosen cell line, while the second plasmid would possess a promoter linked to the luciferase gene in which the response element to the receptor is inserted. If the compound being tested interferes with the receptor-response element pair, transcription of the luciferase gene will be decreased. The resulting chemiluminescence can be measured photometrically. A variation of the foregoing protocol is described in detail in U.S. Pat. No. 4,981,784 and PCT International Publication No. WO 88/03168, for which purpose the artisan is referred. Sometimes a ligand that binds to the receptor may also be required for the receptor to bind the response element of the promoter. In this case, the ligand is also included in the assay.

Detection of the Biological Reactions

When an enzyme is employed in a method of the present invention, the biological reaction it catalyzes generally can be detected by monitoring the loss of substrate and/or the production of a product. Similarly, biological reactions that do not directly involve enzymatic catalysis (e.g., a binding of an antibody to a protein substrate, such as in a Western blot) can be detected indirectly via the use of an enzyme label. Indeed, all of the proteins/peptides (including antibodies and fragments thereof), nucleic acids, and compounds employed in the methods of the invention can be labeled. Suitable labels include enzymes as discussed above, fluorophores (e.g., fluorescein isothiocyanate (FITC), phycoerythrin (PE), Texas red (TR)>rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents.

In the instance where a radioactive label, such as the isotopes, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized techniques known in the art including ultraviolet, visible, and infra-red spectroscopy, circular dichroism, magnetic circular dichroism, fluorescence (including measuring changes in fluorescent lifetimes and fluorescent anisotropy), bioluminescence, luminescence, phosphorescence, mass spectrometry, NMR, ESR, amperometric or gasometric techniques.

Direct labels are one example of labels that can be used according to the present invention. A direct label has been defined as an entity which in its natural state is readily visible, either to the naked eye or with the aid of an optical filter and/or applied stimulation, e.g. ultraviolet light to promote fluorescence. Examples of colored labels that can be used according to the present invention include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, Supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, and urease. These and others have been discussed in detail by Eva Engvall in Enzyme Immunoassay ELISA and EMIT in Methods in Enzymology 70:419–439 (1980) and in U.S. Pat. No. 4,857,453. The protein/peptides of the present invention can be modified to contain a marker protein such as luciferase or green fluorescent protein as described in U.S. Pat. No. 5,625,048 filed Apr. 29, 1997, WO 97/26333, published Jul. 24, 1997 and WO 99/64592, published Dec. 16, 1999, all of which are hereby incorporated by reference in their entireties. Suitable marker enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 by Sidney Pestka, or U.S. Pat. No. 5,459,240.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

High Throughput Assays

The methods of the invention can be performed in a high throughput format using any of a large number of methodologies. One such method employs a solid support that comprises multiple compartments (e.g., wells). Currently a solid support comprising between 96 and 1516 compartments is relatively standard in drug assays. Each compartment can include a separate reaction mixture. In a particular embodiment, a selected target molecule (e.g., an enzyme) can be introduced into the compartments either in solution or on a solid support such as a chip. The remaining components of the reaction mixture can be added to the compartment and a compound can then be added to determine if the enzyme reaction is inhibited by the compound. For example, the enzymatic conversion of a particular cofactor (and/or substrate) to its corresponding product can be measured, e.g., the oxidation of the cofactor NADH to $NAD^+$ by DHFR can be monitored by either ultraviolet-visible spectrometry or by fluorescence.

A given reaction can be performed with a chip (see U.S. Pat. No. 5,874,219, the contents of which are hereby specifically incorporated by reference in its entirety). For example, a nucleotide probe can be placed on chips which are then placed into one or more compartments of the solid substrate. A complementary nucleic acid can then be added to the compartments. A test compound (e.g., a false positive candidate) can be added to one or more of these compartments. The effect of the compound on the binding of the complementary nucleic acid to the nucleotide probe can then be determined. In a particular assay the complementary nucleic acid can have a detectable label. A chip reader is generally used to measure the reaction. Accordingly, the compartments in which the detectable signal intensifies, remains the same, or decreases, can be readily identified. The interaction between reactants can be characterized in a number of ways including in terms of kinetics and/or thermodynamics. As disclosed herein, the solid support preferably contains multiple unrelated biological reactions for testing the false positive candidate, e.g., another compartment could contain a labeled antibody along with its corresponding protein target on a chip. Alternatively, multiple solid substrates can be used, each of which comprising a single type of biological reaction.

Assays on biological arrays generally include carrying out the particular biological reactions under selected conditions, optionally washing the compartment to remove unreacted molecules, and analyzing the biological array for evidence of reaction between the reactants. Since the process can involve multiple steps, it is preferred that such steps be automated so as to allow multiple assays to be performed concurrently. Accordingly high throughput analysis can employ automated fluid handling systems for concurrently performing the reaction steps in each of the compartments. Fluid handling allows uniform treatment of samples in the compartments. Microtiter robotic and fluid-handling devices are commercially available, including from Tecan AG.

A fluid handling device can be used to manipulate the reaction conditions in any given compartment by, for example, (i) adding or removing fluid from the compartments, including for manipulating the concentration of the enzyme; (ii) maintaining and/or manipulating the temperature of the liquid in the compartment; (iii) altering the ionic strength of the reaction mixture; and (iv) agitating the compartments to ensure proper mixing. A reader can then be used to measure the reaction and a computer with an appropriate program can further analyze the results from the reaction (see U.S. Pat. No. 5,874,219, the contents of which are hereby specifically incorporated by reference in its entirety). Data analysis can include removing "outliers" (data deviating from a predetermined statistical distribution), and calculating the relative reaction activity of each compartment. In a particular embodiment, the resulting data are displayed as an image with color in each region varying according to the amount of detectable activity measured.

The solid support can be introduced into a holder in the fluid-handling device. Preferably the fluid-handling device is a robotic device that is programmed to: (i) set appropriate reaction conditions, such as temperature, and volumes; (ii) to add specific reactants to the compartments; (iii) incubate the reactants for an appropriate time; (iv) remove unreacted reactants; (v) wash the compartments; (vi) add reactants/test compounds as appropriate to the compartments; and (viii) allow the detection of the reaction.

Dynamic Light Scattering

The identity of an aggregative compound can be confirmed by any method normally used in the art to characterize macromolecular assemblies in solution, such as light scattering, gel filtration chromatography or other size exclusion methodology, fluorescence and absorbance spectroscopy, tensiometry, pendant drop shape analysis, refractometry, ultracentrifugation, or electron microscopy. Since light scattering is a non-perturbative method of obtaining information about the size of particles in solution, it is a preferred method for establishing a compound as an aggregative compound. Static light scattering (SLS) obtains measurements on the time scale of seconds; it allows one to determine the radius of hydration of a particle in solution, but it requires that the molecular weight of the particle be known beforehand. In the absence of this information, one can use dynamic light scattering (DLS; a.k.a., quasi-elastic light scattering, QELS) to determine the radius of hydration of a particle. DLS obtains measurements on the order of microseconds, and it takes advantage of the fact that particles in solution display Brownian motion. DLS instruments minimally consist of a laser, a sample chamber, and a detector. Upon interacting with the sample, light from the laser is scattered, and the intensity of scattered light is measured by the detector. Because the intensity depends on the angle between the detector and the laser, the detector angle is a critical parameter for any DLS experiment. In fact, useful physical information can be obtained by performing DLS experiments at a variety of detector angles.

A solution of the false positive candidate is prepared (generally in an aqueous and/or aprotic solvent such as dimethyl sulphoxide (DMSO)) and then appropriately diluted. Multiple measurements for each diameter and intensity value is suggested in order to obtain a mean ± standard deviation. Compounds can be analyzed with a 3 W argon-laser at 514.5 nm with BI-9000 and BI-200 optical systems from Brookhaven Instrument Corporation (Holtsville, N.Y.). Calculation of the mean particle diameter can be performed by any of several available pieces of software, including the cumulant analysis tool of the BI9000AT digital autocorrelator. If the compound absorbs significantly at 514.5 nm, they can be measured with a Beckman-Coulter N4 Plus particle analyzer (Fullerton, Calif.) with a 10 mW, helium-neon laser at 632.8 nm, for example. The particle size can be calculated with the SDP analysis tool included by the manufacturer. For both instruments, the detector angle was 90°, but other angles may also be used. As detailed in the Example below, if the compound forms aggregates (e.g., is an aggregative compound) a well-defined autocorrelation function is obtained with an intensity significantly above background.

Other types of DLS instruments include the DynaPro Molecular Sizing/Dynamic Light Scattering instrument from Protein Solutions, Inc., (Charlottesville, Va.), the DAWN Eos, miniDAWN, and WyattQELS instruments from Wyatt Technology, Inc. (Santa Barbara, Calif.), PD2000 instruments from Precision Detectors, Inc. (Franklin, Mass.), and the LB-500 instrument from Horiba, Ltd. (Kyoto, Japan).

Specific Embodiments

To investigate the unusual, non-drug-like behavior displayed by many screening hits, we first studied 15 small-molecule inhibitors discovered by screening (Table 1). These compounds came from multiple virtual and high-throughput screening projects against a variety of targets, including functionally and structurally diverse enzymes, an RNA segment, and a prion. Regardless of the particular target that each compound was initially shown to inhibit, we found that these 15 molecules were micromolar inhibitors of several unrelated model enzymes, including β-lactamase, chymotrypsin, dihydrofolate reductase (DHFR), and β-galactosidase.

Inhibition by these compounds was time-dependent (Table 2). When inhibitor and β-lactamase were preincubated, the $IC_{50}$ decreased (improved) 2- to over 50-fold compared to the $IC_{50}$ when enzyme and inhibitor were not preincubated. A well-studied competitive inhibitor of β-lactamase was not affected by incubation (Weston et al. (1998) J. Med. Chem. 41:4577–4586).

Many time-dependent, nonspecific inhibitors are thought to form irreversible enzyme adducts (Rishton (1997) Drug Discovery Today 2:382–384). One test for irreversible binding is to incubate the inhibitor and enzyme at high concentrations and then to dilute the incubation mixture to below the apparent $IC_{50}$ of the inhibitor. When this was done with —lactamase and moxalactam, a known irreversible β-lactamase inhibitor (Patera et al. (2000) 122:10504–10512), the enzyme remained fully inhibited upon dilution, as expected. When the same test was performed with the screening hits, full enzyme activity returned after dilution (data not shown). This suggested that inhibition by these nonspecific inhibitors was reversible and did not occur via a covalent adduct.

Another mechanism of nonspecific inhibition is denaturation (Miller et al. (1997) 6:2166–2179). If these screening hits acted as denaturants, their potency should increase with temperature or with the concentration of solvent denaturants such as urea or guanidinium. However, temperature had little effect on inhibition (data not shown), and guanidinium or urea either did not affect or actually reduced inhibition by 2- to 19-fold (Table 3). This seemed inconsistent with a denaturant mechanism of inhibition.

Nonspecific binding is often detected by decreased inhibition in the presence of bovine serum albumin (BSA). Inhibition of β-lactamase, β-galactosidase, or chymotrypsin by six screening hits decreased 4- to over 50-fold in the presence of 0.1 mg/mL BSA (Table 3). These results supported a nonspecific mechanism for these compounds and suggested that inhibition by these molecules might be attenuated by the presence of excess protein.

The first suggestion of a unifying mechanism followed the discovery that the $IC_{50}$ values of all compounds increased (worsened) 4 to over 50-fold when the concentration of one of the model enzymes, β-lactamase, was increased 10-fold, from 1 nM to 10 nM (Table 2). A competitive, reversible inhibitor of β-lactamase was unaffected by the increase in enzyme, consistent with the assumption that an enzyme present at nanomolar concentrations would not significantly affect the free concentration of a well-behaved inhibitor present at micromolar concentrations. All compounds tested for this effect also showed an increase in $IC_{50}$ against chymotrypsin when the concentration of this enzyme was increased 10-fold (data not shown). To account for the extreme sensitivity of these screening hits to the molar ratio of inhibitor to enzyme, we considered the hypothesis that the active inhibitor might be an aggregate of many individual molecules.

To determine if these compounds formed aggregates in water, dynamic light scattering (DLS) was initially performed on aqueous mixtures of nine screening hits (Table 4) and subsequently on 20 other compounds (Table 6). For all of these compounds, the presence of submicron particles with strong scattering intensity was suggested by the large amplitude of the autocorrelation function at the smallest values of π and by the decay of the autocorrelation function over the 10–1000 is time scale (FIG. 1). This was also reflected in the intensity of the scattered light from these compounds: all showed scattering intensities at least an order of magnitude higher than buffer alone (Table 4). The apparent diameter of the particles varied from 95 to 400 nm, depending on the compound. These particles dwarf β-lactamase, DHFR, chymotrypsin, and β-galactosidase, which are 6.5, 5.0, 5.4, and 18.5 nm, respectively, in their longest dimensions. In control experiments, 8-anili-no-1-naphthalene-sulfonic acid (ANS), a dye that is structurally similar to many of the nonspecific inhibitors but does not inhibit the model enzymes and does not assemble into aggregates (Stopa et al. (1998) Biochimie 80:963–968), yielded a low amplitude autocorrelation function that lacked a well-defined decay, suggesting that it did not form particles in solution (FIG. 2 and Table 4). Benzo[b]thiophene-2-boronic acid, a competitive inhibitor of β-lactamase, was also not observed to form particles (Table 4). Our positive control, Congo Red, a dye that has been shown to aggregate in solution and that we found to inhibit the model enzymes (Table 1), did form particles detectable by DLS (Table 4).

Aggregates, such as micelles or vesicles, should be affected by ionic strength. The nonspecific inhibitors decreased in potency by 1 to 2 orders of magnitude against β-lactamase as the concentration of buffer was increased from 5 to 500 mM potassium phosphate (KPi) (Table 5). Concomitantly, the mean diameter of the particles formed by these compounds monotonically increased with the ionic strength (Table 5). The potency of a competitive and reversible inhibitor did not change, suggesting that the changes in ionic strength did not significantly affect the enzyme.

The large size of the aggregates suggested that dialysis membranes would impede them. To investigate this prediction, the screening hits were individually incubated with β-lactamase at a high inhibitor concentration and dialyzed against buffer. As a control, a known reversible and specific inhibitor of β-lactamase was also incubated with the enzyme and dialyzed under the same conditions. Enzyme incubated with the reversible and specific inhibitor recovered full activity after dialysis the inhibitor had equilibrated with the surrounding solution. Conversely, enzyme incubated with nonspecific inhibitors remained fully inhibited (data not shown). Although dilution experiments suggested that inhibition by these nonspecific inhibitors was reversible, inhibition was irreversible by equilibration through dialysis, consistent with the aggregation model.

If these nonspecific inhibitors form aggregates on the 100 nm scale, they should be visible by direct methods. We used transmission electron microscopy (TEM) to visualize the particles formed by two nonspecific inhibitors, tetraiodophenolphthalein and Congo Red. Spherical aggregates ranging from 30 to 200 nm in diameter were observed in solutions of these compounds, consistent with results from DLS on tetra-iodophenolphthalein in the same conditions (mean diameter of 83.2+6.5 nm). Analogues of the fullerene in Table 1 have also been shown to form spherical vesicles by TEM (Cassell et al. (1999) Angew. Chem., Int. Ed. 38:2403–2405). Particles were not observed in a solution of the negative control, ANS, also consistent with results from DLS.

To determine if aggregate-forming nonspecific inhibitors are found in pharmaceutical high-throughput screening databases (Stopa et al. (1998) supra), compounds from the screening library of Pharmacia Corporation were tested (Table 6). These compounds were biased toward molecules that hit in multiple screens against different targets. Of these 30 compounds, 20 inhibited β-lactamase and chymotrypsin with micromolar $IC_{50}$ values. Similar to the nonspecific screening hits described above, inhibition by these pharmaceutical compounds improved when they were incubated with β-lactamase and worsened when the β-lactamase concentration was increased 10-fold. These inhibitors also formed strongly scattering particles detectable by DLS at micromolar concentrations (Table 6). These results suggest that molecules that inhibit enzymes by forming aggregates at micromolar concentrations may be common in pharmaceutical screening databases; such compounds would artificially raise hit rates in high-throughput screens for new drug leads.

An aggregation model is surprising for several reasons, not least because it suggests a single mechanism of action for a diverse group of molecules. Nevertheless, it can be reconciled with the peculiar behavior of many promiscuous inhibitors. An aggregate could interact with many enzymes, accounting for the lack of specificity of these inhibitors. Similarly, an aggregate-based mechanism would explain the flat structure-activity relationships often observed with promiscuous inhibitors. Several factors could result in time-dependent inhibition, including formation of the aggregate, its interaction with the enzyme, and the low concentrations of both aggregate and enzyme. An aggregate could form reversibly and interact reversibly with enzyme; dilution would decrease the aggregate concentration and return active enzyme.

Inhibition by an aggregate species would also be extremely sensitive to the concentration of enzyme. Although the molar ratio of inhibitor to enzyme is roughly 10000:1 in these experiments, the ratio of aggregate particles to enzyme molecules will be much lower. Because of this low ratio, increasing the enzyme 10-fold might easily overwhelm the ability of the aggregate to inhibit the enzyme.

Direct physical measurements also support this model. DLS suggests that these compounds form 65–400 nm particles at concentrations similar to their IC50 values against the model enzymes. These particles increase in apparent size as the ionic strength increases, which should increase the number of monomers in each aggregate but decrease the concentration of the aggregate, which is the inhibitory species. Thus, at higher ionic strength, more compound would be necessary to inhibit the enzyme. This ionic strength effect may also explain the effect of guanidinium on inhibition. Particles in the 100 nm range would also not be expected to passively diffuse through a 10 kDa dialysis membrane. Finally, the model is supported by our TEM observations that two nonspecific inhibitors form spherical aggregates in solution.

The arrangement of molecules inside the aggregates remains a question. The compounds studied here do not resemble molecules typically found in micelles or vesicles, such as charged lipids. Instead, these screening hits are typically hydrophobic, planar, and rigid, with a few decorative polar groups. Preliminary ideas may be found in studies on Congo Red by Skowronek et al. (1998) Biopolymers 46:267–281. They suggest that the dye can self-assemble into highly ordered complexes, driven by stacking of the aromatic rings. A related model is proposed by Auweter et al., for the formation of spherical nanoparticles by β-carotene (Auweter et al. (1999) Angew. Chem., Int. Ed. 38:2188–2191). Their results suggest that β-carotene forms crystallites with an aggregation number on the order of 10 000 molecules. They propose that several "crystallites" associate to form the particle core, which is roughly 120 nm in diameter. Such models provide some initial hypotheses about the nature of the interactions involved in aggregate formation by screening hits and may allow one to set some bounds on the number of monomers in a 65–400 nm particle.

Aggregate-forming inhibitors may be found among both virtual and experimental screening hit lists (Table 1) and are well-represented in the literature (Soichet et al. (1993) Science 259:1445–1450; Sun et al. (1998) 41:2588–2603; Boehm et al. (2000) J. Med. Chem. 43:2664–2674; Ring et al. (1993) Proc. Natl. Acad. Sci. USA 90:3583–3587; Gschwend et al. (1997) Proteins 29:59–67; Filikov et al. (2000) J. Comput-Aided Mol. Des. 14:593–610; Hopkins et al. (2000) Biochemistry 39:2805–2814; Schlein et al. (2001) Biochemistry 40:13520; Perola et al. (2000) 43:401–408; Rudyk et al. (2000) J. Gen. Virol. 81 Pt. 4:1155–1164; Joebert et al. (2001) Proteins 45:136–0143; Wolff et al. (2000) 378:216–223; Matter et al. (1992) Biophys. Res. Commun. 186:624–631; Davies et al. (2000) 351:95–105). These include results from several different computational screening algorithms, as well as hits from both enzyme-based and whole-cell high-throughput assays. Additionally, the results in Table 6 suggest that these compounds may be common in pharmaceutical screening libraries; such nonspecific inhibitors would artificially inflate hit rates in screening for new drug leads. Much effort can be wasted chasing aggregate forming "inhibitors" that are unlikely to be useful biologically. By understanding their mechanism of inhibition, these molecules can be identified rapidly and discarded in favor of classically behaved specific inhibitors.

Following the experiments described herein, a small molecule compound, digitonin, was found to be capable of disrupting aggregate formation. Experiments showed that the addition of digitonin to a solution disrupted aggregate formation and prevented unrelated inhibition from occuring (FIG. 3).

Digitonin, or related compounds, are therefore useful in the method of the invention to diagnose for aggregate formation and provide a simple, inexpensive, and unambiguous diagnostic for distinguishing false positive compounds in a collection of positively-identified compounds. A small molecule compound, such as digitonin, capable of inhibiting aggregate formation can be used in conjunction with any of the methods of the invention disclosed herein to identify a false positive compound previously identified as positive in a screening assay.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Mechanism for the Nonspecific Inhibition of Enzymes by Small Molecules

Materials. AmpC β-lactamase was purified as described (Weston et al. (1998) J. Med. Chem. 41:45774586). Chymotrypsin, chicken liver DHFR, β-galactosidase, cephalothin, N-benzoyl-L-tyrosine-ethyl ester (BTEE), succinyl-ala-ala-pro-phe-p-nitroanilide, reduced β-nicotinamide adenine, dinucleotide phosphate (NADPH), dihydrofolic acid (DHF),O-nitrophenyl-β-D-galactopyranoside (ONPG), oxalic-acid-bis-(salicylaldehyde hydrazide), 4-(4-bromophenylazo)phenol, hexachloro-4-(2,4-dinitro-phenylamino)-4-aza-tricyclo (5.2.1.0-(2,6))dec-ene-dione, tetraiodophenolphthalein, moxalactam, Congo Red, Rose Bengal lactone, palatine chrome black, and quercetin were purchased from Sigma-Aldrich. Cephalothin-G-ester was a gift from Eli Lilly. N1-[5-[(5-chloro-1,3-ben-zothiazol-2-yl)]-1,3,4-thiadiazol-2-yl]-3,4-dichloro and 3-(4-isopropylbenzylidene)indolin-2-one were purchased from Maybridge Chemical; ANS and Vat Red I from TCI. (4-((2,4-Di-fluorophenyl) amino)-3,5-thiazolyl)benzene-1,2-diol was purchased from Menai Organics; 3-[(4-phenoxyanilino)methylene]-2-benzofuran-1 (3H)-one from Bionet; benzo[b]thiophene-2-boronic acid from Lancaster Synthesis; nitrocefin from Oxoid; and tris (dicarboxymethylene) fullerene-C3 from Alexis Biochemicals. BSA was purchased from Calbiochem, guanidinium HCl from Amresco, and urea from Fisher Scientific. All materials were used as supplied by the manufacturer, without further purification.

Molecular Docking. A subset of the 1995/2 Available Chemicals Directory containing 153 536 molecules was docked against the structure of AmpC β-lactamase 35 with the Northwestern version of DOCK3.5 as described by Lorber et al. (1998) Protein Sci. 7:938–950.

Enzyme Assays. Compounds were tested for inhibition of β-lactamase, chymotrypsin, DHFR, and β-galactosidase. Unless otherwise stated, assays were performed in 50 mM KPi buffer, pH 7.0 at 25° C. Stocks of substrates and inhibitors were generally prepared at 10 mM in dimethyl sulfoxide (DMSO). No more than 6% DMSO was present in any assay, and results were controlled for the effect of DMSO. All reactions were monitored on an HP8453 spectrophotometer.

For most β-lactamase assays, inhibitor and 1 nM enzyme were incubated for 5 min, and the reaction was initiated with 100 μM cephalothin (Weston et al. (1998) supra) or 200 μM nitrocefin. For β-lactamase assays without incubation, inhibitor and 100 μM cephalothin or 200 μM nitrocefin were mixed, and the reaction was initiated with 1 nM enzyme. For all assays with a 10-fold increase in β-lactamase, inhibitor and 10 nM enzyme were incubated for 5 min, and the reaction was initiated with 100 μM cephalothin-G-ester, the C3' methyl ester of the cephalothin analogue bearing the penicillin G side chain rather than the thiophene acetamide side chain. Cephalothin-G-ester was used because it was a slower substrate for the enzyme and allowed for the measurement of reaction rate over a 5 min interval, even with a 10-fold increase in enzyme concentration. Hydrolysis was monitored at 265 nm for cephalothin and cephalothin-G-ester and at 482 nm for nitrocefin.

100. For chymotrypsin assays, inhibitor and 28 DM enzyme were incubated for five minutes, and the reaction was initiated with 400 μM BTEE 26 or 200 μM succinyl-ala-ala-pro-phe-p-nitro-anilide. Reaction progress was monitored at 260 nm for BTEE or 410 nm for succinyl-ala-ala-pro-phe-p-nitroanilide. For DHFR assays, inhibitor and 120 nM enzyme were incubated for five minutes, and the reaction was initiated with 100 μM NADPH and 100 μM DHF (Su et al. (2001) Proteins 42:279–293); progress was monitored at 340 nm. For β-galactosidase assays, inhibitor and 4 nM enzyme were incubated for 5 min, and the reaction was initiated with 1 mM ONPG; hydrolysis was monitored at 420 nm. β-Galactosidase incubations and reactions were performed at 37° C.

When used, BSA, guanidinium HCl, or urea was present at 0.1 mg/mL, 0.6 M, or 1 M, respectively, and incubated with enzyme and inhibitor before addition of substrate. The concentrations of guanidinium and urea were well below the $C_m$ values for AmpC β-lactamase (Beadle et al. (1999) Protein Sci. 8:1816–1824).

Dialysis of Inhibitor and Enzyme. Inhibitor at 20 times the $IC_{50}$ or DMSO alone was incubated with 10 nM β-lactamase in 10 kDa dialysis tubing. Ten milliliters of this solution was dialyzed at room temperature against three 1 L volumes of 50 mM KPi buffer, pH 7.0, exchanged hourly. After dialysis, the incubation solution was diluted 10-fold and assayed for β-lactamase activity against 100 μM cephalothin.

Dynamic Light Scattering (DLS). Compounds were generally dissolved to 10 mM in DMSO and diluted with filtered 5, 50, or 500 mM KPi. Most compounds were analyzed with a 3 Wargon-ion laser at 514.4 nm with BI-9000 and BI-200 optical systems from Brookhaven Instrument Corporation. The laser power and integration times were comparable for all experiments on this instrument. Calculation of mean particle diameter was performed by the cumulant analysis tool of a 400-channel BI9000AT digital autocorrelator, with the last eight channels used for baseline calculation. Congo Red and Rose Bengal lactone absorb light at 514.4 nm and therefore were analyzed with a Beckinan-Coulter N4 Plus particle analyzer with a 10 mW helium-neon laser at 632.8 nm; particle size was calculated with the SDP analysis tool included by the manufacturer. For both instruments, the detector angle was 90°. Each diameter and intensity value represents four or more independent measurements at 25° C.

Transmission Electron Microscopy (TEM). Solutions of 100 μM tetraiodophenolphthalein, 50 μM Congo Red, or 625 μM ANS were prepared in 20 mM Tris, pH 7.2. At room temperature, 3 μL of each was applied to a carbon-coated grid and negatively stained with 1% uranyl acetate. Images were obtained with a Philips CM12 transmission electron microscope at 120 kV. Micrographs were recorded at 22000×magnification and 2 μm underfocus.

Table 1: [a]Unpublished observations. [b]$K_d$. [c]maximal non-effective concentration. cDHFR, chicken DHFR; β-gal, β-galactosidase; pDHFR, *Pneumocystis carinii* DHFR; TS, thymidylate synthase; VEGF, vascular endothelial growth factor receptor tyrosine kinase; IGF-1, insulin-like growth factor receptor tyrosine kinase; TIM, triosephosphate isomerase; eNOS, endothelial nitric oxide synthase; nNOS, neuronal nitric oxide synthase; PI3K, phosphoinositide 3-kinase; N.D., not determined.

Table 2: [a]Benzo[b]thiophene-2-boronic acid, a specific, competitive, and reversible inhibitor of AmpC β-lactamase.

Table 3: All guanidinium and urea data were obtained against β-lactamase. [a]Against β-lactamase. [b]Against β-galactosidase. [c]Against chymotrypsin. N.D., not determined.

Table 4: DLS performed in 50 mM $KP_i$ at the concentration given under "DLS conc." [a]A specific, competitive, and reversible inhibitor of AmpC β-lactamase. [b]ANS is known not to aggregate. [c]Compounds analyzed by DLS at 632.8 nm; all others analyzed at 514.4 nm. kcps, kilocounts per second.

Table 5: [a]DLS experiments performed in 5, 50, or 500 mM $KP_i$ at the concentration specified in Table 3. [b]A specific, competitive, and reversible inhibitor of AmpC □-lactamase. [26] [c]Compounds analyzed by DLS at 632.8 nm; all others analyzed at 514.4 nm. N.D., not determined.

Table 6: [a]DLS experiments in 5 mM $KP_i$; all others in 50 mM $KP_i$. [b]Compound absorbs significantly at 514.4 nm. Laser power was comparable in all experiments. chymo., chymotrypsin; N.D., not determined.

TABLE 1

Nonspecific inhibitors discovered by screening.

| Structure | Original Target(s) | IC$_{50}$ ($\mu$M) | | | |
|---|---|---|---|---|---|
| | | β-lactamase | Chymo-trypsin | cDHFR | β-gal |
| [structure: 5-chlorobenzothiazole-thiadiazole-dichlorobenzamide] | β-lactamase[a] | 0.5 | 2.5 | 5 | 15 |
| | 0.5 | | | | |
| [structure: hydroxyphenyl-azo-bromophenyl] | β-lactamase[a] | 5 | 25 | 35 | 90 |
| | 5 | | | | |
| [structure: isobenzofuranone-phenoxyaniline] | β-lactamase[a] | 5 | 15 | N.D. | N.D. |
| | 5 | | | | |
| [structure: bis(hydroxybenzylidene) oxalyl dihydrazide] | malarial protease[14] | 10 | 55 | 70 | 180 |
| | 8 | | | | |
| [structure: bis-benzothiophene dione] | pDHFR[15] | 10 | 50 | 60 | 300 |
| | 7 | | | | |
| [structure: naphthol azo naphthol sulfonate] | pDHFR[15] | 50 | 25 | N.D. | 600 |
| | 80 | | | | |

TABLE 1-continued

Nonspecific inhibitors discovered by screening.

| Structure | Original Target(s) | IC$_{50}$ ($\mu$M) | | | |
|---|---|---|---|---|---|
| | | β-lactamase | Chymo-trypsin | cDHFR | β-gal |
| | 50<br>HIV Tar RNA[16] | 10 | 90 | N.D. | 600 |
| | 3<br>TS[8]   30<br>kinesin[17] | 3 | 11 | 20 | 200 |
| | 20[b]<br>insulin receptor[18]   7.5<br>kinesin[17] | 16 | 50 | N.D. | 80 |
| | 5.2<br>VEGF[9]   10.0<br>IGF-1[9] | 6 | 30 | 30 | 55 |
| | 25<br>farnesyltransferase[19] | 3 | 9 | 25 | 150 |

TABLE 1-continued

Nonspecific inhibitors discovered by screening.

| Structure | Original Target(s) | IC$_{50}$ ($\mu$M) β-lactamase | Chymo-trypsin | cDHFR | β-gal |
|---|---|---|---|---|---|
| 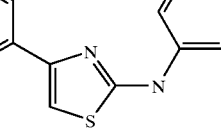 | 15$^c$ gyrase$^{10}$ | 18 | 100 | 150 | 320 |
| 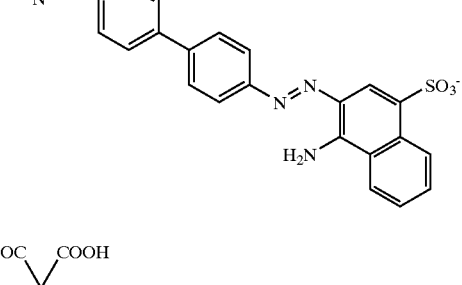 | 1 prion$^{20}$ | 30.4 TIM$^{21}$ | 3.9 | 40 | 0.4 | 100 |
|  | 17 eNOS$^{22}$ | 24 nNOS$^{22}$ | 7 | 60 | N.D. | N.D. |
| 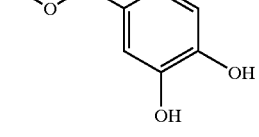 | 3.8 PI3K$^{23,24}$ | 11.0 integrase$^{25}$ | 4 | 100 | N.D. | 220 |

TABLE 2

The effect of incubation or a ten-fold increase in enzyme concentration on inhibition of β-lactamase.

| Structure | ↓ IC$_{50}$ with Incubation | ↑ IC$_{50}$ vs. 10x Enzyme |
|---|---|---|
|  $^a$ | No change | No change |

TABLE 2-continued

The effect of incubation or a ten-fold increase in enzyme concentration on inhibition of β-lactamase.

| Structure | ↓ IC$_{50}$ with Incubation | ↑ IC$_{50}$ vs. 10x Enzyme |
|---|---|---|
| (structure) | 6-fold | 7-fold |
| (structure) | 23-fold | 23-fold |
| (structure) | 4-fold | 40-fold |
| (structure) | 22-fold | 40-fold |
| (structure) | 32-fold | 6-fold |
| (structure) | 6-fold | 7-fold |
| (structure) | 3-fold | 4-fold |

TABLE 2-continued

The effect of incubation or a ten-fold increase in enzyme concentration on inhibition of β-lactamase.

| Structure | ↓ IC$_{50}$ with Incubation | ↑ IC$_{50}$ vs. 10x Enzyme |
|---|---|---|
| (structure) | 7-fold | >50-fold |
| (structure) | 3-fold | 22-fold |
| (structure) | >50-fold | >50-fold |
| (structure) | 44-fold | 22-fold |
| (structure) | 9-fold | 7-fold |

TABLE 2-continued

The effect of incubation or a ten-fold increase in enzyme concentration on inhibition of β-lactamase.

| Structure | ↓ $IC_{50}$ with Incubation | ↑ $IC_{50}$ vs. 10x Enzyme |
|---|---|---|
| 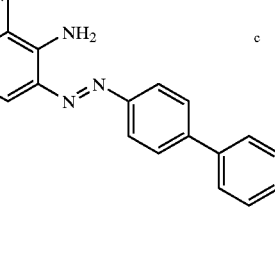 c | 11-fold | 15-fold |
| 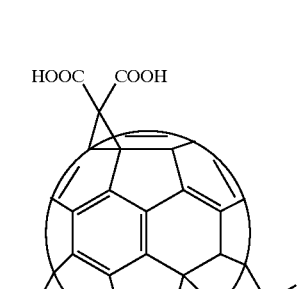 | 2-fold | >50-fold |
| 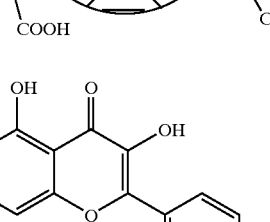 | 2-fold | >50-fold |

TABLE 3

The effect of guanidinium, urea, or BSA on inhibition of β-lactamase, β-galactosidase, or chymotrypsin.

| | ↑ $IC_{50}$ in the presence of | | |
|---|---|---|---|
| Structure | GndHCl | Urea | BSA |
|  | 3-fold | No effect | >50-fold[a]<br>>50-fold[b]<br>>50-fold[c] |

TABLE 3-continued

The effect of guanidinium, urea, or BSA on inhibition of β-lactamase, β-galactosidase, or chymotrypsin.

| | ↑ IC$_{50}$ in the presence of | | |
|---|---|---|---|
| Structure | GndHCl | Urea | BSA |
| 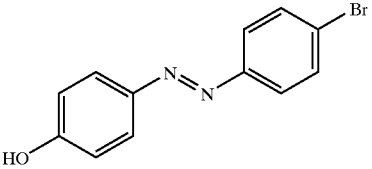 | 6-fold | 2-fold | 8-fold[b]<br>18-fold[c] |
| 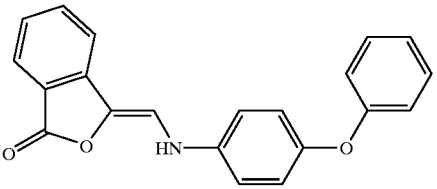 | 3-fold | 7-fold | >50-fold[a]<br>9-fold[b]<br>12-fold[c] |
| 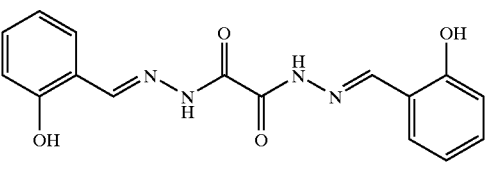 | 6-fold | 4-fold | >50-fold[a]<br>4-fold[c] |
| 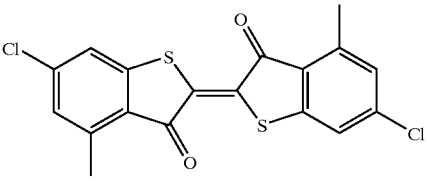 | 19-fold | 3-fold | 12-fold[a]<br>6-fold[c] |
| 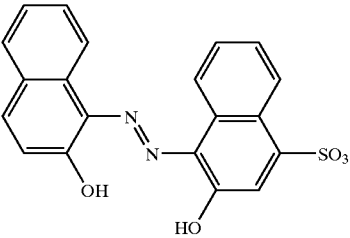 | 4-fold | N.D. | >50-fold[a]<br>>50-fold[c] |

TABLE 4

Dynamic light scattering reveals that several nonspecific inhibitors form particles.

| Structure | IC$_{50}$ vs. β-lactamase (μM) | DLS conc. (μM) | Intensity (kcps) | Diameter (nm) |
|---|---|---|---|---|
| 50 mM KP$_i$ | — | — | 0.4 ± 0.1 | No particles |
| 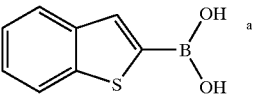 a | 0.2 | 100 | 0.9 ± 0.2 | No particles |

TABLE 4-continued
Dynamic light scattering reveals that several nonspecific inhibitors form particles.
| Structure | IC$_{50}$ vs. β-lactamase (μM) | DLS conc. (μM) | Intensity (kcps) | Diameter (nm) |
|---|---|---|---|---|
| 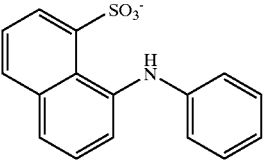 b | >1600 | 1000 | 0.5 ± 0.1 | No particles |
| 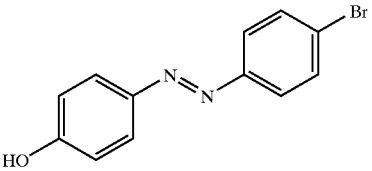 | 5 | 10 | 12.6 ± 3.9 | 176.2 ± 7.9 |
| 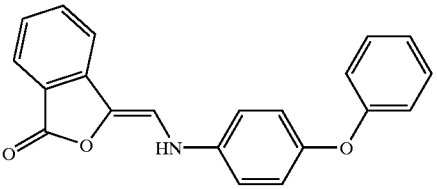 | 5 | 100 | 16.2 ± 1.1 | 94.7 ± 4.2 |
| 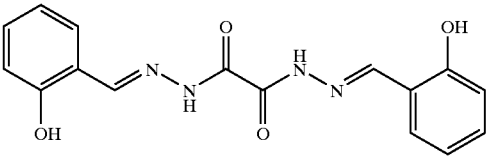 | 10 | 10 | 26.4 ± 5.1 | 394.6 ± 12.5 |
| 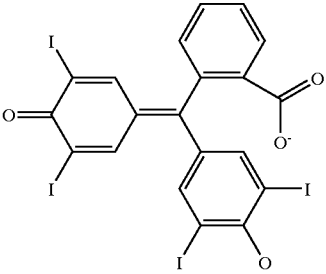 | 3 | 10 | 42.2 ± 3.9 | 153.4 ± 26.0 |
| 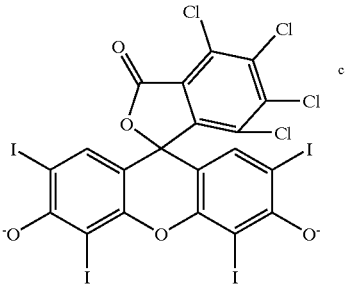 c | 16 | 500 | 115.1 ± 65.6 | 403.1 ± 82.2 |

TABLE 4-continued

Dynamic light scattering reveals that several nonspecific inhibitors form particles.

| Structure | IC$_{50}$ vs. β-lactamase (μM) | DLS conc. (μM) | Intensity (kcps) | Diameter (nm) |
|---|---|---|---|---|
| 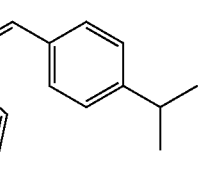 | 6 | 10 | 43.8 ± 5.7 | 379.0 ± 14.1 |
| 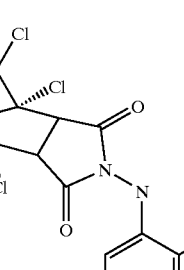 | 3 | 15 | 24.9 ± 3.1 | 418.6 ± 38.8 |
| 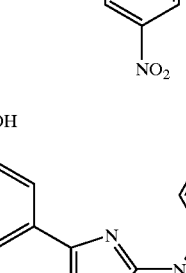 | 18 | 300 | 32.3 ± 4.3 | 165.1 ± 10.9 |
| 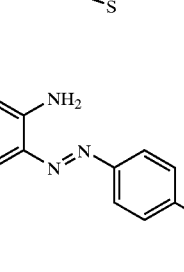 c | 3.9 | 750 | 131.1 ± 64.3 | 202.6 ± 22.5 |

TABLE 5

Effect of ionic strength on inhibition and aggregate size.

| | IC$_{50}$ vs. β-lactamase (μm) | | | Diameter (nm)$^a$ | | |
|---|---|---|---|---|---|---|
| Structure | 5 mM KP$_i$ | 50 mM KP$_i$ | 500 mM KP$_i$ | 5 mM KP$_i$ | 50 mM KP$_i$ | 500 mM KP$_i$ |
|  b | 0.2 | 0.2 | 0.3 | No particles | No particles | No particles |

TABLE 5-continued

Effect of ionic strength on inhibition and aggregate size.

| | IC$_{50}$ vs. β-lactamase (μm) | | | Diameter (nm)[a] | | |
|---|---|---|---|---|---|---|
| Structure | 5 mM KP$_i$ | 50 mM KP$_i$ | 500 mM KP$_i$ | 5 mM KP$_i$ | 50 mM KP$_i$ | 500 mM KP$_i$ |
| (naphthalene with SO$_3^-$ and NH-phenyl) | >1600 | >1600 | >1600 | No particles | No particles | No particles |
| (HO-phenyl-N=N-phenyl-Br) | 2.3 | 5 | 12 | 140.2 ± 12.1 | 176.2 ± 7.9 | 267.4 ± 24.5 |
| (bis-salicylaldehyde oxalyl dihydrazone) | 4 | 10 | 15 | 389.3 ± 55.4 | 394.6 ± 12.5 | 426.6 ± 23.8 |
| (tetraiodophenolphthalein) | 1 | 3 | 5 | 86.2 ± 10.5 | 153.4 ± 26.0 | 320.4 ± 38.8 |
| (tetrachloro-tetraiodo-fluorescein derivative)[c] | 0.47 | 16 | 19 | N.D. | 403.1 ± 82.2 | N.D. |
| (isopropylbenzylidene oxindole) | 3 | 6 | 7 | 247.1 ± 12.8 | 379.0 ± 14.1 | 494.3 ± 48.1 |

TABLE 5-continued

Effect of ionic strength on inhibition and aggregate size.

| Structure | IC$_{50}$ vs. β-lactamase (μm) | | | Diameter (nm)[a] | | |
|---|---|---|---|---|---|---|
| | 5 mM KP$_i$ | 50 mM KP$_i$ | 500 mM KP$_i$ | 5 mM KP$_i$ | 50 mM KP$_i$ | 500 mM KP$_i$ |
| 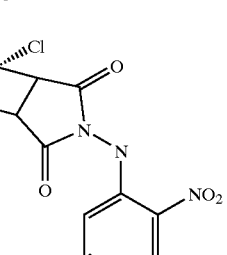 | 0.5 | 3 | 6 | 143.5 ± 7.9 | 418.6 ± 38.8 | N.D. |
| 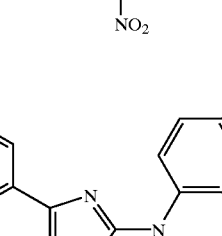 | 3 | 18 | 133 | 102.9 ± 9.9 | 165.1 ± 10.9 | 436.2 ± 24.8 |
| 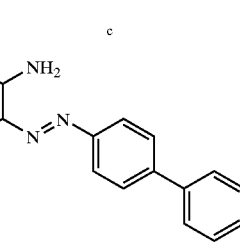 | 0.65 | 3.9 | 340 | N.D. | 202.6 ± 22.5 | N.D. |

TABLE 6

Nonspecific inhibition and aggregation by compounds from the Pharmacia screening library.

| Structure | IC$_{50}$ vs. β-lactamase (μM) | ↓ IC$_{50}$ with Incubation | ↑ IC$_{50}$ vs. 10x β-lactamase | IC$_{50}$ vs. chymo. (μM) |
|---|---|---|---|---|
| 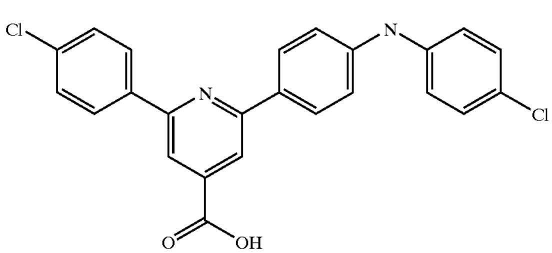 | 2 | 12-fold | 4-fold | 2 |

TABLE 6-continued

Nonspecific inhibition and aggregation by compounds from the Pharmacia screening library.

| Structure | # | | | |
|---|---|---|---|---|
| (structure) | 4 | >50-fold | 12-fold | 13 |
| (structure) | 5 | 35-fold | 10-fold | 8 |
| (structure) | 8 | 24-fold | 20-fold | 15 |
| (structure) | 15 | >50-fold | 5-fold | 3 |
| (structure) | 50 | >50-fold | 4-fold | 50 |

TABLE 6-continued
Nonspecific inhibition and aggregation by compounds from the Pharmacia screening library.
| Structure | | | | |
|---|---|---|---|---|
| 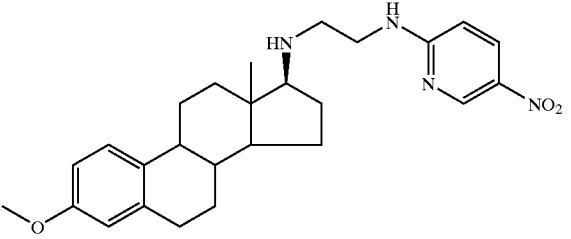 | 5 | 14-fold | >50-fold | 13 |
| 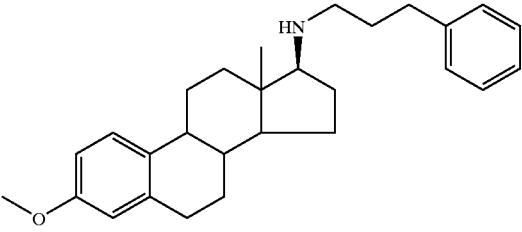 | 5 | >50-fold | >50-fold | 200 |
| 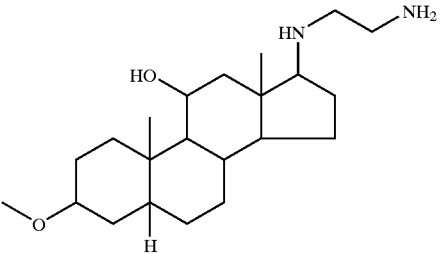 | 10 | 4-fold | 4-fold | 40 |
| 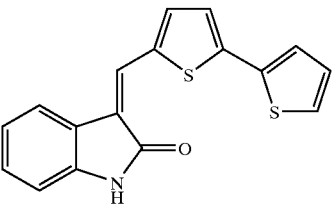 | 2 | 13-fold | 8-fold | 15 |
| 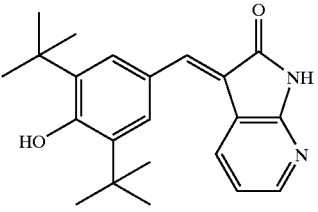 | 4 | >50-fold | 6-fold | 10 |
| 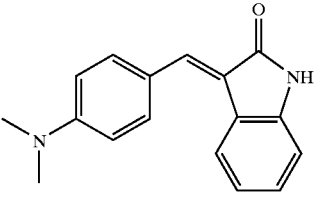 | 10 | >50-fold | 3-fold | 30 |

TABLE 6-continued

Nonspecific inhibition and aggregation by compounds from the Pharmacia screening library.

| Structure | | | | |
|---|---|---|---|---|
| [tetrahydronaphthalene-methyl-oxindole with OH] | 15 | 3-fold | 6-fold | 40 |
| [chlorobenzothiazole-thio-thiadiazole-thiophene amide] | 2 | >50-fold | 3-fold | 15 |
| [bromophenyl-azo-hydroxyphenyl] | 15 | 5-fold | >50-fold | 220 |
| [bis(chloro-methyl-benzothiophenone)] | 3 | 15-fold | 3-fold | 15 |
| [disulfonated bis-azo naphthalenediol with bromo groups] | 80 | 2-fold | >50-fold | 110 |
| [bromo-hydroxynaphthalene-azo-phenoxyacetic acid] | 30 | >50-fold | 8-fold | 80 |
| [benzyloxyphenyl sulfonyl phenoxy heptanoic acid] | 3 | 7-fold | 9-fold | 13 |

TABLE 6-continued
Nonspecific inhibition and aggregation by compounds from the Pharmacia screening library.
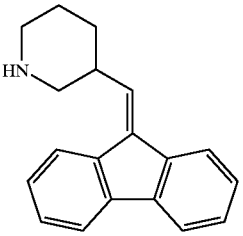
| | 200 | 2-fold | >50-fold | 700 |
| | | DLS | | |
|---|---|---|---|---|
| Structure | Conc. (μM) | Intensity (kcps) | Diameter (nm) | |
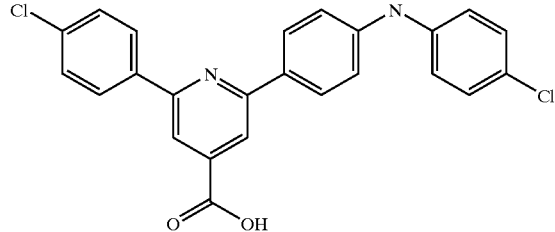
| | 50 | 54.3 ± 5.5 | 100.4 ± 5.1 |
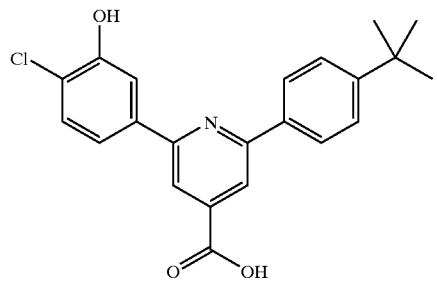
| | 50 | 24.4 ± 2.6 | 97.1 ± 2.5 |
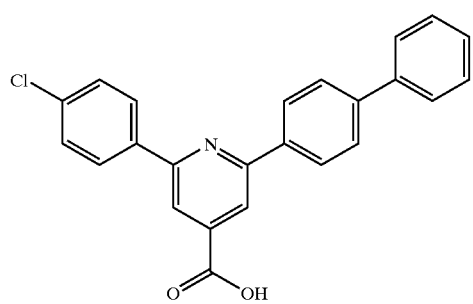
| | 80[a] | 19.2 ± 4.7 | 171.8 ± 35.8 |
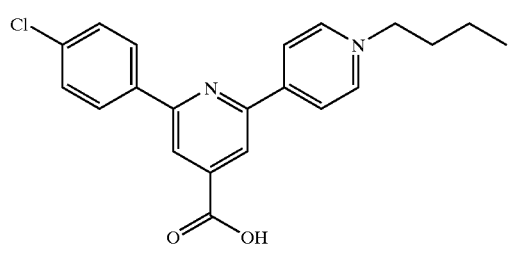
| | 50 | 11.1 ± 2.4 | 106.9 ± 6.3 |

TABLE 6-continued
Nonspecific inhibition and aggregation by compounds from the Pharmacia screening library.
| Structure | | | |
|---|---|---|---|
| 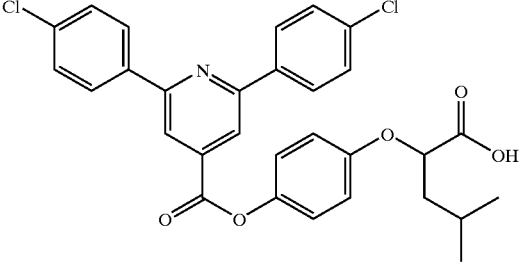 | 50 | 30.4 ± 2.5 | 108.5 ± 5.1 |
| 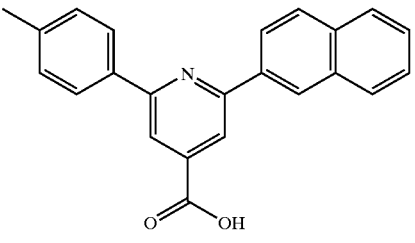 | 500[a] | 13.5 ± 3.4 | 201.2 ± 44.4 |
| 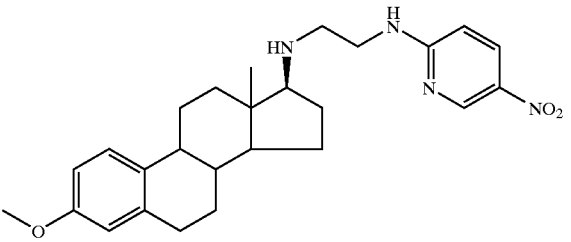 | 40[a] | 20.2 ± 0.8 | 381.0 ± 30.4 |
| 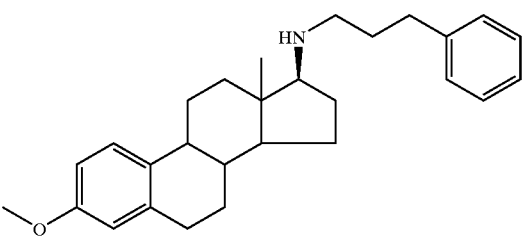 | 100 | 8.0 ± 0.6 | 297.4 ± 19.9 |
| 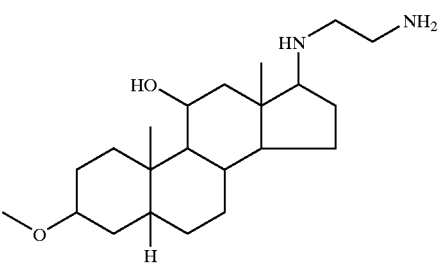 | 100 | 10.0 ± 1.9 | N.D. |
| 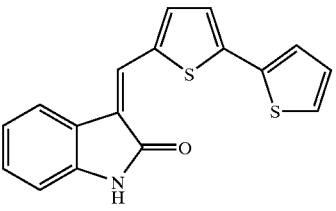 | 20 | 12.6 ± 4.3 | N.D. |

TABLE 6-continued

Nonspecific inhibition and aggregation by compounds from the Pharmacia screening library.

| Structure | Conc | Value 1 | Value 2 |
|---|---|---|---|
| (3,5-di-tert-butyl-4-hydroxybenzylidene)-7-azaoxindole | 10[a] | 14.2 ± 1.1 | 140.9 ± 9.0 |
| (4-dimethylaminobenzylidene)oxindole | 30[a] | 51.2 ± 7.2 | 288.6 ± 21.8 |
| 3-((5,6,7,8-tetrahydronaphthalen-2-yl)methyl)-4-hydroxyoxindole | 40 | 14.0 ± 5.9 | N.D. |
| 5-chloro-2-((5-(thiophene-2-carboxamido)-1,3,4-thiadiazol-2-yl)thio)benzothiazole | 15 | 17.5 ± 1.8 | 172.5 ± 9.2 |
| 4-((3-bromophenyl)diazenyl)phenol | 500 | 10.5 ± 2.5 | 184.4 ± 25.6 |
| 6,6'-dichloro-4,4'-dimethylthioindigo | 20 | 10.0 ± 0.3 | 205.8 ± 5.7 |
| bis-azo naphthalene sulfonate dye | —[b] | —[b] | —[b] |

TABLE 6-continued

Nonspecific inhibition and aggregation by compounds from the Pharmacia screening library.

| | | | |
|---|---|---|---|
| [structure: brominated naphthol azo phenoxyacetic acid] | 20 | 19.6 ± 2.7 | N.D. |
| [structure: benzyloxy diphenyl sulfone heptanoic acid] | 500[a] | 3.0 ± 0.4 | 68.2 ± 7.6 |
| [structure: piperidine fluorenylidene] | 100 | 16.7 ± 1.2 | 221.0 ± 4.2 |

What is claimed is:

1. A method of identifying a false positive compound previously identified as a positive compound in a screening assay, comprising:
   (a) measuring the activity of a first biological reaction in the presence and absence of the compound in the presence of a small molecule capable of inhibiting aggregate formation; and
   (b) measuring the activity of the first biological reaction in the presence and absence of the compound in the absence of a small molecule capable of inhibiting aggregate formation; wherein a false positive compound is identified as capable of inhibiting the biological activity in the absence, but not the presence, of the small molecule compound.

2. The method of claim 1, wherein the small molecule compound is selected from the group consisting of digitonin, saponin, polymixin B, amphotericin, nystatin, an aminoglycoside, and Triton X-100™.

3. The method of claim 2, wherein the small molecule compound is digitonin.

4. The method of claim 1, wherein step (a) and step (b) are repeated to measure the activity of an unrelated second biological reaction.

* * * * *